United States Patent [19]
Young

[11] Patent Number: 5,462,435
[45] Date of Patent: Oct. 31, 1995

[54] ADJUSTABLE MOUTH PROP

[76] Inventor: James P. Young, 1527 Jacqueline Dr., Holt, Mich. 48842

[21] Appl. No.: 199,710

[22] Filed: Feb. 22, 1994

[51] Int. Cl.⁶ ..................................................... A61C 5/00
[52] U.S. Cl. .......................... 433/140; 600/245; 600/238
[58] Field of Search ................................. 433/31, 93, 136, 433/138, 140; 128/12, 13, 15, 17, 18, 14

[56] References Cited

U.S. PATENT DOCUMENTS

| 742,698 | 10/1903 | Mason | 128/17 |
| 815,907 | 3/1906 | Davis | 128/17 |
| 1,094,575 | 4/1914 | Joutras | 128/18 |
| 2,061,936 | 11/1936 | Engelfried | 128/12 |
| 2,075,534 | 3/1937 | McCormack | 128/17 |

FOREIGN PATENT DOCUMENTS 20374 of 1903 United Kingdom ..................... 128/17

Primary Examiner—Cary E. O'Connor

[57] ABSTRACT

A new and improved adjustable mouth prop for holding a dental patient's mouth open during performance of a dental procedure in a manner which is safe and comfortable for the patient and convenient for the dentist is disclosed. The adjustable mouth prop comprises a threaded shaft formed of rigid material suitable for sterilization, the shaft having an enlarged head formed on one end thereof. Upper and lower arms formed of rigid material suitable for sterilization are mounted on the threaded shaft and project outwardly from the threaded shaft. The distal end of the arms have integral elongated concave jaw support members extending laterally thereacross. The jaw support members are engagable with the patient's teeth such that the teeth are removedly retained irrespective of the angles of the arms. The adjustable mouth prop further includes adjustable locking member whereby the user may lock the arm members at a selected angular position relative to each other to prop open the patient's mouth. Sterile cushioning pad members are disposed over the jaw support members. The cushioning pad members comprises an outer elastic covering removably stretched over the jaw support member and a resilient molding material disposed within the covering filling the cavity of the jaw support member to comfortably and securely contact a patient's teeth. The new and improved adjustable mouth prop may additionally include a light source attached to the lower arm to illuminate the mouth of the patient.

8 Claims, 4 Drawing Sheets

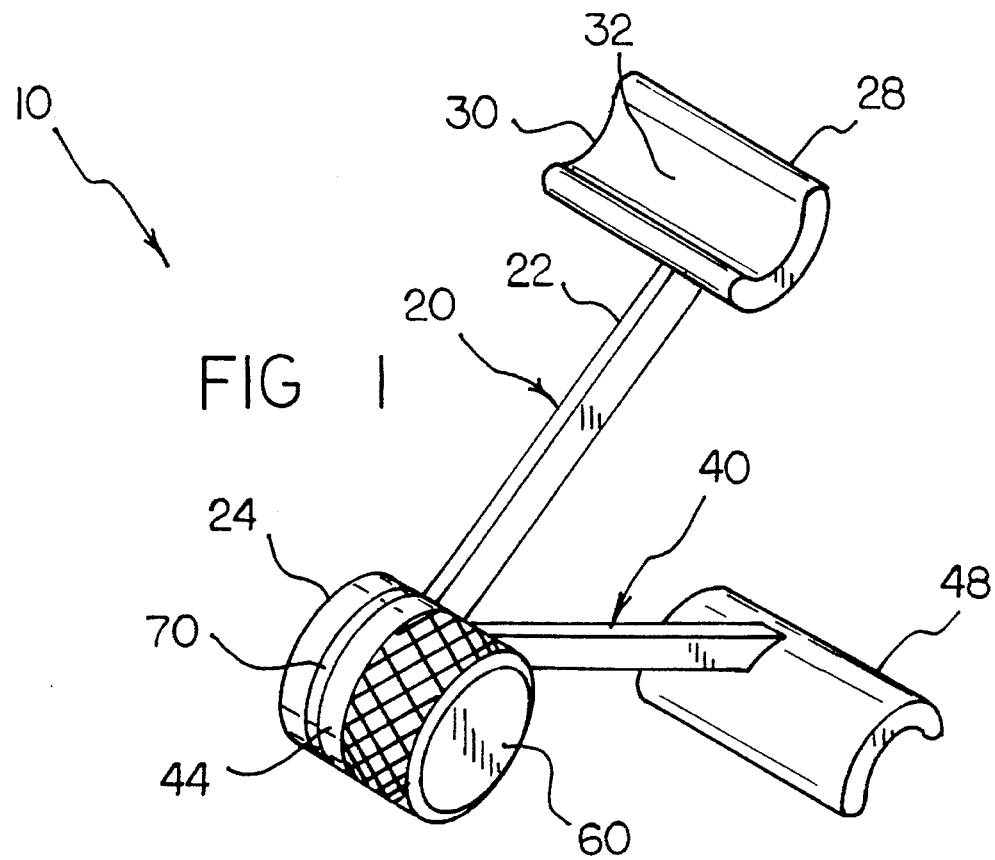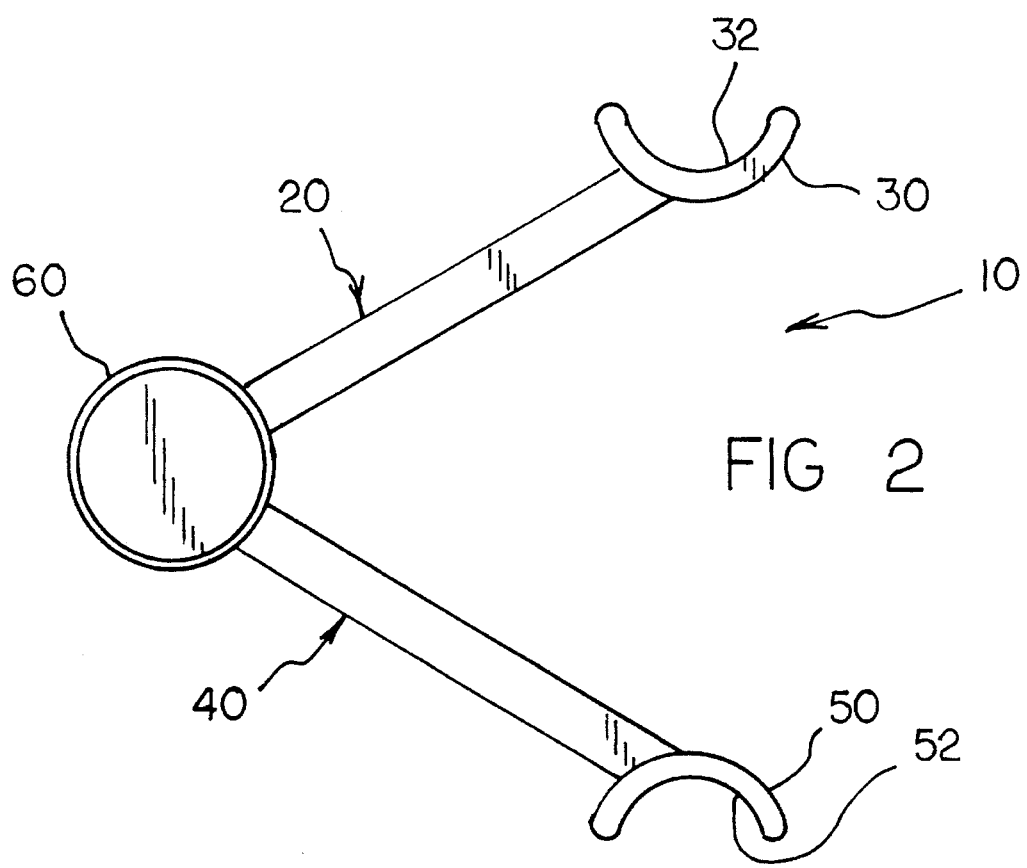

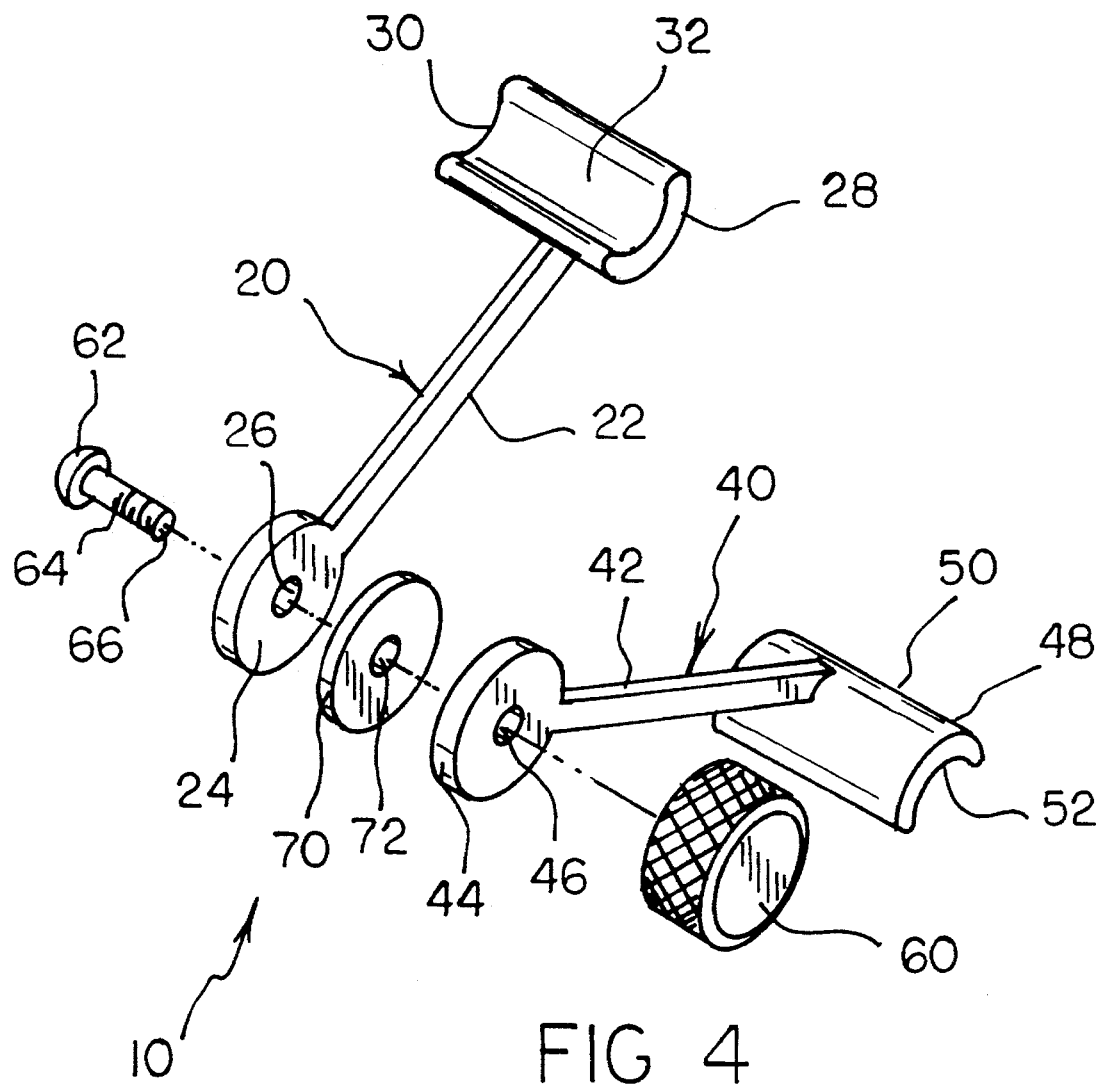

ADJUSTABLE MOUTH PROP

BACKGROUND OF THE INVENTION

1. Field of the Invention

The present invention relates to mouth props and more particularly pertains to adjustable mouth props which may be adapted for holding a dental patient's mouth open during performance of a dental procedure in a manner which is safe and comfortable for the patient and convenient for the dentist.

2. Description of the Prior Art

The use of mouth props is known in the prior art. More specifically, mouth props heretofore devised and utilized for the purpose of holding a dental patient's mouth open during performance of a dental procedure are known to consist basically of familiar, expected and obvious structural configurations, notwithstanding the myriad of designs encompassed by the crowded prior art which have been developed for the fulfillment of countless objectives and requirements.

The present invention is directed to improving devices for holding a dental patient's mouth open during performance of a dental procedure in a manner which is safe, secure, economical and aesthetically pleasing.

For example, U.S. Pat. No. 4,991,566 to Shulman et al. discloses a an articulating mouth-prop device for use in the diagnosis and/or treatment of patients suffering from trismus or other medical or dental problems or for other purposes. The device includes a pair of outwardly-extending upper arms and a pair of outwardly extending lower arms. Each of the arms has a respective distal end which has a pad mounted thereon which contacts the patient's jaws during use thereof, and a respective proximal end which is secured to the housing. Members are provided for pivoting the distal ends of the upper arms towards and away from the distal end of the lower arms such that the distal ends move substantially arcuately between the open and closed positions. A worm and worm wheel arrangement is provided for pivoting the arms, such that the spacing therebetween is infinitely variable. The invention disclosed is complex and bulky making it difficult to use and uncomfortable for the patient.

U.S. Pat. No. 4,887,965 to Fox describes an adjustable mouth prop having jaw engaging plates connected by a spring. The plates hold a resilient molding material to comfortably and securely contact a patient's teeth. The plates are further connected by an adjusting mechanism which is used to adjust and maintain a controlled occlusal opening. The adjusting mechanism is made of a screw extending from each plate and an internally threaded sleeve connecting the two screws. The sleeve is threaded to either draw together or separate the screws and their attached jaw engaging plates, thereby closing or opening the occlusal opening. This sleeve and screw adjusting mechanism allows for easy and gradual adjustment of the size of the occlusal opening, without disruption of the dental procedure or discomfort to the patient. The sleeve and screw adjusting mechanism of this invention is located inside the patient's mouth during use which may interfere with some dental procedures. Also, the sleeve is not captive on the device, leading to the possibility of it becoming disconnected during use and swallowed by the patient.

The prior art also discloses a dental rest for jaws in an open bite position as shown in U.S. Pat. No. 3,483,619 to Smith, a mouth prop described in U.S. Pat. No. 4,053,984 to Moss, and a dental mouth prop disclosed in U.S. Pat. No. 5,009,595 to Osborn. While these devices fulfill their respective, particular objectives and requirements, the three patents mentioned above do not disclose a adjustable mouth prop for holding a dental patient's mouth open during performance of a dental procedure.

In this respect, the adjustable mouth prop according to the present invention substantially departs from the conventional concepts and designs of the prior art, and in so doing provides an apparatus primarily developed for the purpose of holding a dental patient's mouth open during performance of a dental procedure in a manner which is safe and comfortable for the patient and convenient for the dentist.

Therefore, it can be appreciated that there exists a continuing need for new and improved adjustable mouth props which can be used for holding a dental patient's mouth open during performance of a dental procedure in a manner which is safe and comfortable for the patient and convenient for the dentist. In this regard, the present invention substantially fulfills this need.

As illustrated by the background art, efforts are continuously being made in an attempt to develop devices for holding a dental patient's mouth open during performance of a dental procedure. No prior effort, however, provides the benefits attendant with the present invention. Additionally, the prior patents and commercial techniques do not suggest the present inventive combination of component elements arranged and configured as disclosed and claimed herein.

The present invention achieves its intended purposes, objects, and advantages through a new, useful and unobvious combination of method steps and component elements, with the use of a minimum number of functioning parts, at a reasonable cost to manufacture, and by employing only readily available materials.

SUMMARY OF THE INVENTION

In view of the foregoing disadvantages inherent in the known types of mouth props now present in the prior art, the present invention provides an improved mouth prop construction wherein the same can be utilized for holding a dental patient's mouth open during performance of a dental procedure in a manner which is safe and comfortable for the patient and convenient for the dentist. As such, the general purpose of the present invention, which will be described subsequently in greater detail, is to provide a new and improved adjustable mouth prop apparatus and method which has all the advantages of the prior art mouth props and none of the disadvantages.

The invention is defined by the appended claims with the specific embodiment shown in the attached drawings. For the purpose of summarizing the invention, the invention may be incorporated into a new and improved adjustable mouth prop for holding a dental patient's mouth open during performance of a dental procedure in a manner which is safe and comfortable for the patient and convenient for the dentist. The adjustable mouth prop comprises a threaded shaft formed of rigid material suitable for sterilization, the shaft having an enlarged head formed on one end thereof. An upper arm formed of rigid material suitable for sterilization is also included. The upper arm is mounted on the threaded shaft and projects upwardly and outwardly perpendicularly from the threaded shaft. The distal end of the upper arm has an integral elongated upwardly opening concave upper jaw support member extending laterally thereacross. The upper jaw support member is engagable with the patient's upper teeth such that the teeth are removably retained within the cavity irrespective of the elevational angle of the arm. The proximal end of the upper arm has an integral discus bearing surface formed radially thereon. The center of the bearing surface has a lateral hole therethrough whereby the arm is mounted on the threaded shaft.

Also included in the new and improved adjustable mouth prop is a lower arm formed of rigid material suitable for sterilization. The lower arm is pivotally mounted on the threaded shaft and projects downwardly and outwardly perpendicularly from the threaded shaft. The distal end of the lower arm has an integral elongated downwardly opening concave lower jaw support member extending laterally thereacross. The lower jaw support member is engagable with the patient's lower teeth such that the teeth are removedly retained within the cavity irrespective of the declinational angle of the arm. The proximal end of the lower arm has an integral discus bearing surface formed radially thereon. The center of the bearing surface has a lateral hole therethrough whereby the arm is mounted on the threaded shaft.

The adjustable mouth prop further includes a lock washer formed of rigid material suitable for sterilization. The lock washer is disposed on the threaded shaft between the bearing surfaces of the arms, in cooperative relationship with the bearing surfaces such that the arms may be locked angularly with respect to each other when the proximal ends of the arms are biased toward each other to bring the bearing surfaces into touching facing contact with the lock washer. The lock washer is also in cooperative relationship with the bearing surfaces such that the arms may pivot freely with respect to each other when the proximal ends of the arms are unbiased whereby positioning the bearing surfaces in spaced facing relationship with the lock washer.

The new and improved adjustable mouth prop also has a knurled thumbnut formed of rigid material suitable for sterilization. The thumbnut threadedly engages the free end of the threaded shaft such that rotating the nut in one direction biases the proximal ends of the upper and lower arms together into contact with the lock washer, and rotating the nut in the opposite direction releases the bias.

The new and improved adjustable mouth prop further includes sterile cushioning pad means disposed over the upper and lower concave jaw support members. The cushioning pad means comprises an outer elastic covering removably stretched over the jaw support member and a resilient molding material disposed within the covering filling the cavity of the jaw support member to comfortably and securely contact a patient's teeth.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In as much as the foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the disclosed specific methods and structures may be readily utilized as a basis for modifying or designing other structures for carrying out the same purposes of the present invention. It should be realized by those skilled in the art that such equivalent methods and structures do not depart from the spirit and scope of the invention as set forth in the appended claims.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Therefore, it is an object of the present invention to provide an adjustable mouth prop for holding a dental patient's mouth open during performance of a dental procedure in a manner which is safe and comfortable for the patient and convenient for the dentist.

It is therefore an additional object of the present invention to provide a new and improved adjustable mouth prop which has all the advantages of the prior art mouth props and none of the disadvantages.

It is another object of the present invention to provide a new and improved adjustable mouth prop which may be easily and efficiently manufactured and marketed.

It is a further object of the present invention to provide a new and improved adjustable mouth prop which is of a durable and reliable construction.

An even further object of the present invention is to provide a new and improved adjustable mouth prop which is susceptible of a low cost of manufacture with regard to both materials and labor, and which accordingly is then susceptible of low prices of sale to the consuming public, thereby making such adjustable mouth props economically available to the buying public.

Still yet another object of the present invention is to provide a new and improved adjustable mouth prop which provides in the apparatuses and methods of the prior art some of the advantages thereof, while simultaneously overcoming some of the disadvantages normally associated therewith.

Still yet another object of the present invention is to provide a new and improved adjustable mouth prop that is of minimal size to allow maximum access to the patient's mouth.

Yet another object of the present invention is to provide a new and improved adjustable mouth prop of a design that is suitable for use with a wide variety of patients, under diverse conditions, without requiring modification.

Even still another object of the present invention is to provide a new and improved adjustable mouth prop that may be sterilized by means of any technique commonly used for sterilization of dental instruments.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention. The foregoing has outlined some of the more pertinent objects of this invention. These objects should be construed to be merely illustrative of some of the more prominent features and applications of the present invention. Many other beneficial results can be attained by applying the disclosed invention in a different manner or by modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the new and improved adjustable mouth prop.

FIG. 2 is a side elevational view of the invention of FIG. 1.

FIG. 3 is a top plan view of the invention of FIG. 1.

FIG. 4 is an exploded perspective view of the invention of FIG. 1 showing its component parts.

DESCRIPTION OF THE PREFERRED EMBODIMENT

Figure 5:
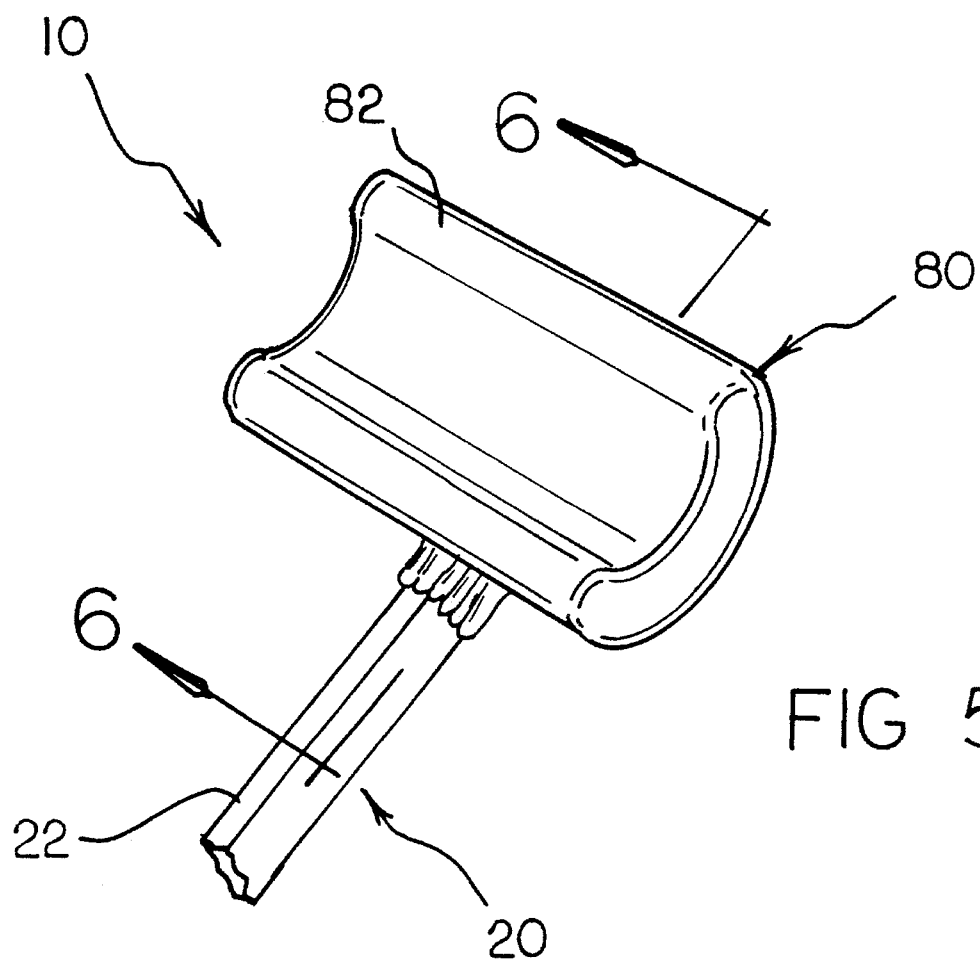
FIG. 5 is a perspective view of the cushioning pad showing its manner of use.

With reference now to the drawings, and in particular to FIG. 1 thereof, a new and improved adjustable mouth prop embodying the principles and concepts of the present invention and generally designated by the reference numeral 10 will be described.

From an overview standpoint, the adjustable mouth prop is adapted for use for holding a dental patient's mouth open during performance of a dental procedure in a manner which is safe and comfortable for the patient and convenient for the dentist. See FIG. 1.

With reference now to FIGS. 1–4 and more specifically, it will be noted that a new and improved adjustable mouth prop 10 for holding a dental patient's mouth open during performance of a dental procedure in a manner which is safe and comfortable for the patient and convenient for the dentist is shown. The adjustable mouth prop 10 comprises a threaded shaft 64 formed of rigid material suitable for sterilization, the shaft 64 having an enlarged head 62 formed on one end thereof.

An upper arm 20 formed of rigid material 22 suitable for sterilization is also included. The upper arm 20 is mounted on the threaded shaft 64 and projects upwardly and outwardly perpendicularly from the threaded shaft 64. The distal end of the upper arm 20 has an integral elongated upwardly opening concave upper jaw support member 30 28 or extending laterally thereacross. The upper jaw support member 30 is engagable with the patient's upper teeth such that the teeth are removedly retained within the cavity 32 irrespective of the elevational angle of the arm 20.

The proximal end of the upper arm 20 has an integral discus bearing surface 24 formed radially thereon. The center of the bearing surface 24 has a lateral hole 26 therethrough whereby the arm 20 is mounted on the threaded shaft 64.

Also included in the new and improved adjustable mouth prop 10 is a lower arm 40 formed of rigid material 42 suitable for sterilization. The lower arm 40 is pivotally mounted on the threaded shaft 64 and projects downwardly and outwardly perpendicularly from the threaded shaft 64. The distal end of the lower arm 40 has an integral elongated downwardly opening concave lower jaw support member 48 or 50 extending laterally thereacross. The lower jaw support member 50 is engagable with the patient's lower teeth such that the teeth are removedly retained within the cavity 52 irrespective of the declinational angle of the arm 40.

The proximal end of the lower arm 40 has an integral discus bearing surface 44 formed radially thereon. The center of the bearing surface 44 has a lateral hole 46 therethrough whereby the arm is mounted on the threaded shaft 64.

The adjustable mouth prop 10 further includes a lock washer 70 formed of rigid material suitable for sterilization. The lock washer 70 having an aperture 72 extending therethrough is disposed on the threaded shaft 64 between the bearing surfaces 24 and 44 of the arms 20 and 40, in cooperative relationship with the bearing surfaces 24 and 44 such that the arms 20 and 40 may be locked angularly with respect to each other when the proximal ends of the arms are biased toward each other to bring the bearing surfaces 24 and 44 into touching facing contact with the lock washer 70.

The lock washer 70 is also in cooperative relationship with the bearing surfaces 24 and 44 such that the arms 20 and 40 may pivot freely with respect to each other when the proximal ends of the arms are unbiased whereby positioning the bearing surfaces 24 and 44 in spaced facing relationship with the lock washer 70.

The new and improved adjustable mouth prop 10 also has a knurled thumbnut 60 formed of rigid material suitable for sterilization. The thumbnut 60 threadedly engages the free end 66 of the threaded shaft such that rotating the nut 60 in one direction biases the bearing surfaces 24 and 44 of the upper and lower arms 20 and 40 together into contact with the lock washer 70, and rotating the nut 60 in the opposite direction releases the bias.

Figure 6:
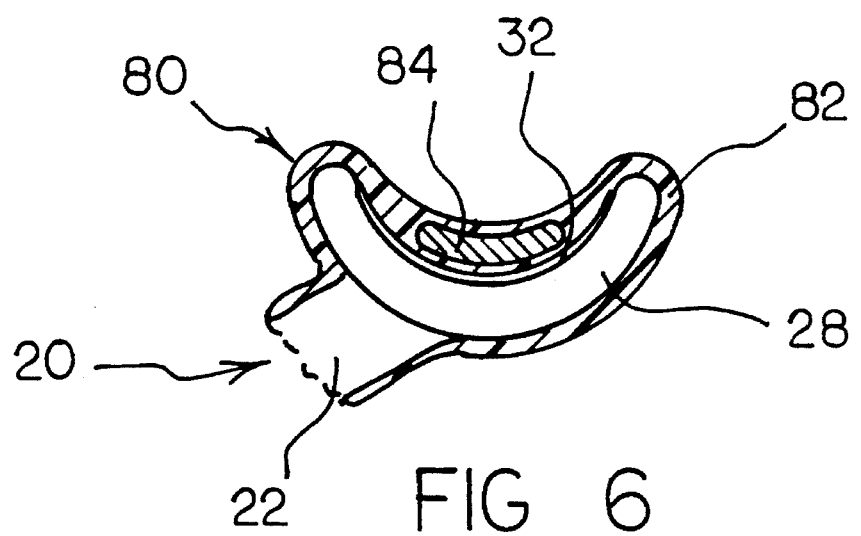
FIG. 6 is a sectional view of the invention of FIG. 5 taken along the line 6—6.

Referring additionally to FIGS. 5 and 6, the new and improved adjustable mouth prop 10 further includes sterile cushioning pad means 80 disposed over the upper and lower concave jaw support members 30 and 50. The cushioning pad means 80 comprises an outer elastic covering 82 removably stretched over the jaw support members 30 and 50 and a resilient molding material 84 disposed within the covering 82 filling the cavity 32 and 52 of the jaw support member 30 and 50 to comfortably and securely contact a patient's teeth.

Figure 7:
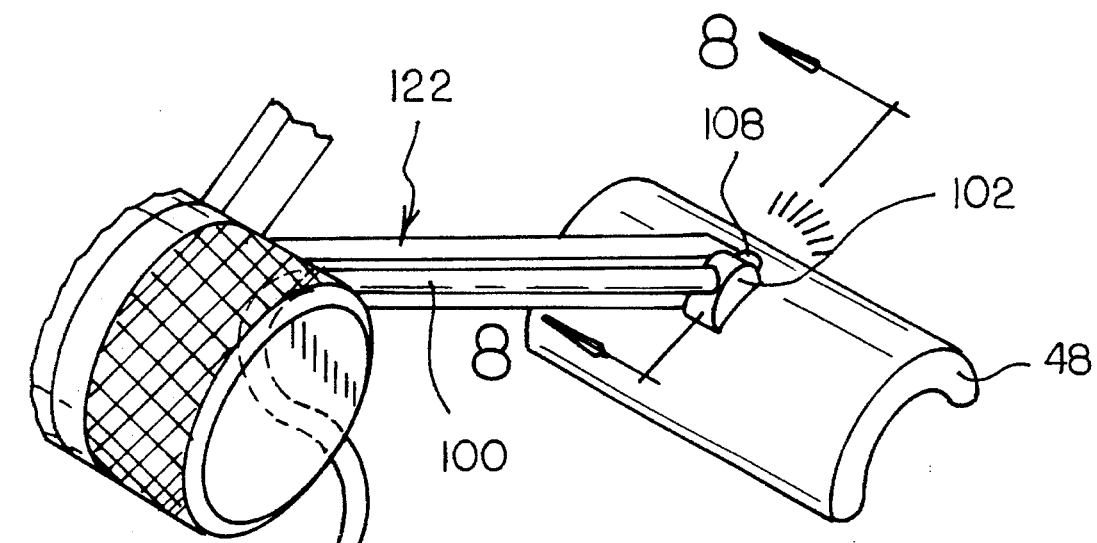
FIG. 7 is a partial perspective view of an alternate embodiment of the present invention illustrating a light source with a fiber optic transmission line attached to the lower arm of the adjustable mouth prop of FIG. 1.
Figure 8:
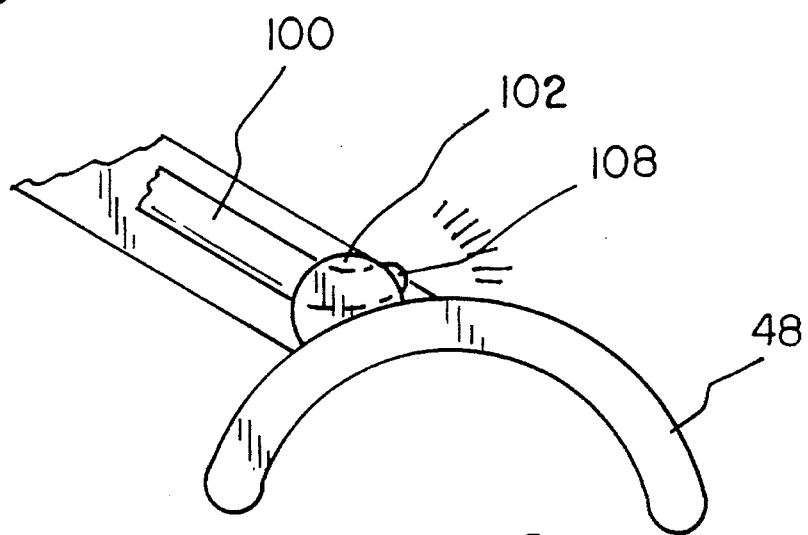
FIG. 8 is a detail view of a manner of attachment of the fiber optic transmission line to the lower jaw engagement member of the present invention.

In an alternate embodiment shown in FIGS. 7 and 8 and generally referred to by the reference numeral 120, the new and improved adjustable mouth prop 120 additionally includes fiber optic transmission line attachment means 102 fixedly connected to the distal end of the lower arm 122. A first end 104 of a fiber optic transmission line 100 is optically coupled to a remotely located light source 106. The fiber optic transmission line 100 extends from the remote light source 106 to the proximal end of the adjustable mouth prop lower arm 122 whereto it is fixedly connected.

The fiber optic transmission line 100 extends longitudinally along the lower arm 122 to terminate at the attachment means 102 such that the mouth of the patient may be illuminated from end 108 of the optic transmission line 100 during use of the mouth prop 120.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. In as much as the present disclosure includes that contained in the appended claims as well as that of the foregoing description. Although this invention has been described in its preferred forms with a certain degree of particularity, it is understood that the present disclosure of the preferred form has been made only by way of example and numerous changes in the details of construction and combination and arrangement of parts may be resorted to without departing from the spirit and scope of the invention.

Now that the invention has been described,
What is claimed is:

1. A new and improved adjustable mouth prop for holding a dental patient's mouth open during performance of a dental procedure in a manner which is safe and comfortable for the patient and convenient for the dentist, the adjustable mouth prop comprising:

a threaded shaft formed of rigid material suitable for sterilization, the shaft having an enlarged head formed on one end thereof;

an upper arm formed of rigid material suitable for sterilization, the upper arm mounted on the threaded shaft, the upper arm projecting upwardly outwardly perpendicularly from the threaded shaft, the distal end of the upper arm having an integral elongated upwardly opening concave upper jaw support member extending laterally thereacross, the upper jaw support member being engageable with the patient's upper teeth such that the teeth are removedly retained within the cavity irrespective of the elevational angle of the arm, the proximal end of the upper arm having an integral discus bearing surface formed radially thereon, the center of the bearing surface having a lateral hole therethrough whereby the arm is mounted on the threaded shaft;

a lower arm formed of rigid material suitable for sterilization, the lower arm pivotally mounted on the threaded shaft, the lower arm projecting downwardly outwardly perpendicularly from the threaded shaft, the distal end of the lower arm having an integral elongated downwardly opening concave lower jaw support member extending laterally thereacross, the lower jaw support member being engageable with the patient's lower teeth such that the teeth are removedly retained within the cavity irrespective of the declinational angle of the arm, the proximal end of the lower arm having an integral discus bearing surface formed radially thereon, the center of the bearing surface having a lateral hole therethrough whereby the arm is mounted on the threaded shaft;

a lock washer formed of rigid material suitable for sterilization, the lock washer being disposed on the threaded shaft between the bearing surfaces of the arms, the lock washer also being in cooperative relationship with the bearing surfaces such that the arms may be locked angularly with respect to each other when the proximal ends of the arms are biased toward each other to bring the bearing surfaces into touching facing contact with the lock washer, the lock washer also being in cooperative relationship with the bearing surfaces such that the arms may pivot freely with respect to each other when the proximal ends of the arms are unbiased to position the bearing surfaces in spaced facing relationship with the lock washer; and a knurled thumbnut formed of rigid material suitable for sterilization, the thumbnut threadedly engaging the free end of the threaded shaft such that rotating the nut in one direction biases the proximal ends of the upper and lower arms together into contact with the lock washer, and rotating the nut in the opposite direction releases the bias.

2. The new and improved adjustable mouth prop of claim 1 and further including sterile cushioning pad means disposed over the upper and lower concave jaw support members, the cushioning pad means comprising an outer elastic covering removably stretched over the jaw support member; and a resilient molding material disposed within the covering filling the cavity of the jaw support member to comfortably and securely contact a patient's teeth.

3. The new and improved adjustable mouth prop of claim 2 and further including a light source attached to the lower arm to illuminate the mouth of the patient.

4. A new and improved adjustable mouth prop for holding a dental patient's mouth open during performance of a dental procedure in a manner which is safe and comfortable for the patient and convenient for the dentist, the adjustable mouth prop comprising:

a shaft member formed of a rigid material suitable for sterilization, said shaft member being threaded and including an enlarged head formed at one end thereof;

an upper arm member mounted on the shaft member, the distal end of the upper arm member having an upper jaw support member extending therefrom, the upper jaw member being engagable with the patient's upper teeth;

a lower arm member pivotally mounted on the shaft member, the distal end of the lower arm member having a lower jaw support member extending therefrom, the lower jaw support member being engagable with the patient's lower teeth, said arm members being formed of a rigid material suitable for sterilization;

adjustable locking means whereby the user can lock the arm members at a selected annular position relative to each other to prop open the patient's mouth, wherein said jaw support members comprise integral opposed concave elongated retainers wherein the patient's teeth can be engaged irrespective of the relative angle of the arm members;

bearing surfaces formed on the proximal end of each arm member;

a lock washer disposed on the threaded shaft between the bearing surfaces of the arm members, the lock washer being in cooperative relationship with the bearing surfaces such that the arm members may be locked angularly with respect to each other when the proximal ends of the arm members are biased toward each other to bring the bearing surfaces into touching facing contact with the lock washer, the lock washer also being in cooperative relationship with the bearing surfaces such that the arm members may pivot freely with respect to each other when the proximal ends of the arm members are not biased toward each other thereby positioning the bearing surfaces in spaced facing relationship with the lock washer; and a knurled thumbnut formed of rigid material suitable for sterilization, the thumbnut threadedly engaging the free end of the threaded shaft such that rotating the nut in one direction biases the proximal ends of the upper and lower arms together into contact with the lock washer, and rotating the nut in the opposite direction releases the bias.

5. The adjustable mouth prop of claim 4 wherein the bearing surfaces are disc-shaped, and the center of each bearing surface has a lateral hole therethrough whereby the arm member is mounted on the shaft member.

6. The adjustable mouth prop of claim 5 wherein the lock washer is formed of rigid material suitable for sterilization.

7. The new and improved adjustable mouth prop of claim 6 and further including sterile cushioning pad means disposed over the upper and lower concave support members, the cushioning pad means comprising an outer elastic covering removably stretched over the support member; and a resilient molding material disposed within the covering filling the cavity of the support member to comfortably and securely contact a patient's teeth.

8. The new and improved adjustable mouth prop of claim 7 and further including a light source attached to the lower arm to illuminate the mouth of the patient.

* * * * *